US012589377B2

(12) United States Patent
Aussant

(10) Patent No.: US 12,589,377 B2
(45) Date of Patent: Mar. 31, 2026

(54) ENCAPSULATED COMPOSITION COMPRISING CORE-SHELL MICROCAPSULES AND PROCESS FOR ITS PREPARATION

(71) Applicant: GIVAUDAN SA, Vernier (CH)

(72) Inventor: Emmanuel Aussant, Paris (FR)

(73) Assignee: GIVAUDAN SA, Vernier (CH)

( * ) Notice: Subject to any disclaimer, the term of this patent is extended or adjusted under 35 U.S.C. 154(b) by 658 days.

(21) Appl. No.: 17/922,111

(22) PCT Filed: May 25, 2021

(86) PCT No.: PCT/EP2021/063932
§ 371 (c)(1),
(2) Date: Oct. 28, 2022

(87) PCT Pub. No.: WO2021/239742
PCT Pub. Date: Dec. 2, 2021

(65) Prior Publication Data
US 2023/0166230 A1       Jun. 1, 2023

(30) Foreign Application Priority Data

May 26, 2020    (GB) ..................................... 2007795

(51) Int. Cl.
*B01J 13/14* (2006.01)
*A61K 8/11* (2006.01)
*B01J 13/10* (2006.01)
*C11D 3/50* (2006.01)

(52) U.S. Cl.
CPC ................. *B01J 13/14* (2013.01); *A61K 8/11* (2013.01); *B01J 13/10* (2013.01); *C11D 3/505* (2013.01); *A61K 2800/412* (2013.01)

(58) Field of Classification Search
CPC ....................................................... A61K 8/11
See application file for complete search history.

(56) References Cited

U.S. PATENT DOCUMENTS

| | | | | |
|---|---|---|---|---|
| 3,888,689 | A * | 6/1975 | Maekawa .............. | C09D 11/03 |
| | | | | 106/31.54 |
| 4,317,743 | A * | 3/1982 | Chang ...................... | B01J 13/06 |
| | | | | 427/151 |
| 4,908,233 | A * | 3/1990 | Takizawa ................. | B01J 13/08 |
| | | | | 427/213.36 |
| 2013/0330292 | A1* | 12/2013 | Lei .......................... | A61K 8/731 |
| | | | | 424/70.17 |
| 2015/0250689 | A1* | 9/2015 | Dardelle ................ | C11D 3/505 |
| | | | | 264/4.1 |
| 2018/0228702 | A1* | 8/2018 | Aussant .................... | A61K 8/25 |
| 2019/0240124 | A1* | 8/2019 | Dardelle ................. | A61K 8/87 |
| 2020/0360244 | A1* | 11/2020 | Lei .......................... | C11D 3/225 |
| 2022/0071865 | A1* | 3/2022 | Sasaki ..................... | A61Q 15/00 |
| 2022/0226208 | A1* | 7/2022 | Lei .......................... | A61K 8/11 |
| 2022/0226797 | A1* | 7/2022 | Popplewell ......... | C08B 37/0096 |
| 2025/0011691 | A1* | 1/2025 | Aussant ................. | C11D 3/128 |

FOREIGN PATENT DOCUMENTS

| | | | | | |
|---|---|---|---|---|---|
| GB | | 1141186 | A * | 1/1969 | ............. A01N 25/28 |
| WO | WO-2015023961 | A1 * | 2/2015 | ............. A61Q 19/00 |

OTHER PUBLICATIONS

Duhoranimana et al. (Food Hydrocolloids 69 (2017) 111-120) (Year: 2017).*
Roy et al. (Carbohydrate Polymers 198, 2018, 281-293) (Year: 2018).*
Yang et al. (Food Chemistry 135 2012 555-561) (Year: 2012).*

* cited by examiner

*Primary Examiner* — Liam J Heincer
(74) *Attorney, Agent, or Firm* — Norris McLaughlin, PA

(57) ABSTRACT

The present invention relates to a process for obtaining an encapsulated composition, to encapsulated compositions obtainable by this process, to products comprising these encapsulated compositions and to the use of these encapsulated compositions to provide consumer products.

29 Claims, No Drawings

ENCAPSULATED COMPOSITION COMPRISING CORE-SHELL MICROCAPSULES AND PROCESS FOR ITS PREPARATION

This is an application filed under 35 USC 371 based on PCT/EP2021/063932, filed May 25, 2021, which claimed priority to GB 2007795.4 filed May 26, 2020. The present application claims the full priority benefit of all prior applications and incorporates by reference their full disclosures as if set forth herein.

The present invention relates to a process for obtaining an encapsulated composition, to an encapsulated composition obtainable by such a process and to a use of such an encapsulated composition to provide a consumer product.

It is known to incorporate encapsulated functional materials in consumer products, such as household care, personal care and fabric care products. Functional materials include for example fragrances, cosmetic actives, and biologically active ingredients, such as biocides and drugs.

Microcapsules that are particularly suitable for delivery of such functional materials are core-shell microcapsules, wherein the core comprises the functional material and the shell is impervious or partially impervious to the functional material. Usually, these microcapsules are used in aqueous media and the encapsulated functional materials are hydrophobic. A broad selection of shell materials can be used provided this shell material is impervious or partially impervious to the encapsulated functional material.

Among the functional materials, fragrances are encapsulated for a variety of reasons. Microcapsules can isolate and protect the fragrances from external suspending media, such as consumer product bases, with which they may be incompatible or unstable in. They are also used to assist in the deposition of fragrance ingredients onto substrates, such as skin, hair, fabrics or hard household surfaces. They can also act as a means of controlling the spatio-temporal release of the fragrance.

Thermosetting resins are common encapsulating materials for encapsulating functional materials, especially volatile functional materials, such as fragrance ingredients. Core-shell microcapsules formed from aminoplast resins, polyurea resins, polyurethane resins, polyacrylate resin, and combinations thereof are generally quite resistant to fragrance leakage when dispersed in aqueous suspending media, even in surfactant-containing media. Furthermore, when incorporated into consumer products, such as laundry detergents or conditioners, they provide perfumery benefits that are unattainable if perfume is incorporated directly into those products.

However, nowadays consumers are increasingly concerned about using materials obtained from non-renewable sources, such as synthetic petrochemicals. In other words, consumers tend to favor materials the origin of which is more sustainable in terms of environment and resource protection. Nevertheless, it is generally difficult to use natural materials or materials derived from nature to address all aspects of benefit agent encapsulation. In particular, the means of forming capsules that can encapsulate with high encapsulation efficiency and that are sufficiently impervious to benefit agents during storage has proved to be elusive.

For instance, protein-based and especially gelatin-based core-shell microcapsules are well known to the art. Gelatin-based microcapsules are conventionally obtained by a so-called coacervation process, wherein a complex between gelatin and a polysaccharide is formed at the core/water interface. Coacervation is then followed by cross-linking, in order to stabilize the shell mechanically and thermally.

Cross-linking may be achieved by using a broad selection of cross-linking agents, provided the cross-linking reaction may occur at the oil/water interface, meaning in the presence of water. Cross-linking reactions that are effective in water involve, for example, reactions between available primary amine groups of gelatin with formaldehyde, di-aldehydes, and resorcinol.

WO 2018/002214 A1 discloses the use of polyisocyanates to cross-link the gelatin-gum Arabic coacervate forming the shell of fragrance-containing microcapsules. A principal issue encountered with such cross-linked coacervate is their tendency to swell in water-based products and to become permeable to the encapsulated functional material. This is particularly true if the functional core material is a low-molecular weight material, i.e. materials having a molecular weight lower than 250 g/mol, such as fragrance ingredients. Furthermore, the median size of microcapsules obtained in WO 2018/002214 A1 is in the order of 600 μm, meaning the microcapsules may be visible to the eye, either in consumer products or on substrates. This limits drastically their use as perfume delivery systems in consumer products.

These issues have considerably hampered the development of protein-based microcapsules for fragrance encapsulation.

It is therefore a problem underlying the present invention to overcome the above-mentioned shortcomings in the prior art. In particular, it is a problem underlying the present invention to provide protein-based encapsulated compositions of the above-mentioned kind showing improved stability during manufacture, storage and in application. Furthermore, the compositions should be producible in an operationally safe, robust and cost-efficient process.

These problems are solved by the subject-matter of the independent claims.

In a first aspect, the present invention relates to a process for obtaining an encapsulated composition comprising a plurality of core-shell microcapsules. The core-shell microcapsules comprise a core and a shell surrounding the core. The shell is formed by cross-linking of at least one protein with a first cross-linking agent, followed by the addition of at least one polysaccharide to form a complex coacervate.

The core of the core-shell microcapsules is made of a core composition. The core composition is essentially water-immiscible.

By "essentially water-immiscible" it is meant that, when the core composition admixed with water, even under intensive stirring, at least 95 wt.-%, preferably at least 99 wt.-%, of the core composition phase separates from the water phase, either immediately or progressively after the cessation of the stirring.

Preferably, the amount of core composition is lower than the amount of aqueous phase, so that, when emulsified with the aqueous phase, the core composition forms a dispersed phase in the aqueous phase, generally in the form of core composition droplets.

In context of the present invention, cross-linking of at least one protein with a first cross-linking agent leads to the formation of a stable core composition emulsion, comprising a plurality of core composition droplets. These stabilize the emulsion in that it prevents the droplets from coalescing. These stabilized droplets act as templates on which the microencapsulation further takes place.

Without being bound to any theory, the cross-linking reaction of the at least one protein with the first cross-linking agent can occur as interfacial polymerization at the core composition-water phase interface, in order to form a first shell around the core composition droplets, or by formation of a simple coacervate, as described further herein below. Also a continuum between these two processes is possible.

In particular embodiments of the present invention, the shell is formed by cross-linking of the at least one protein with the first cross-linking agent in order to form a simple coacervate.

By "coacervate" it is meant polyelectrolyte-rich droplets coexisting with an aqueous, polyelectrolyte poor continuous phase. The droplets can agglomerate at interfaces to form an interfacial layer.

In the present context, the coacervate droplets agglomerate at the interface between the core composition and the aqueous phase. As a result, a stable core composition emulsion in water is formed, comprising a plurality of core composition droplets, each droplet being surrounded by coacervate droplets. These stabilize the emulsion in that it prevents the droplets from coalesce.

By "simple coacervation" is meant in the present context the formation of an interfacial layer comprising a single polyelectrolyte.

By "complex coacervation" is meant the formation of an interfacial layer comprising a mixture of polyelectrolytes.

The phenomenon of simple or complex coacervation may be observed under a light microscope, wherein it is marked by the appearance of a ring around the core composition droplet. This ring consists of the aforementioned polyelectrolyte-rich phase that has a different refractive index than the surrounding aqueous phase.

The coacervation of a single polyelectrolyte is generally induced by bringing the polyelectrolyte to its isoelectric point, meaning the point where the net charge of the polyelectrolyte is zero or close to zero. This may be achieved by changing the salt concentration or, in the case of a poly-ampholyte, such as proteins, by changing the pH of the medium.

The applicant has found that simple coacervation may also be induced by cross-linking a protein at the core composition/water interface.

It has been found that building first a cross-linked protein, in particular as simple coacervate, at the core composition/aqueous phase interface, followed by the complex coacervation of this cross-linked protein with a second polyelectrolyte, namely at least one polysaccharide, leads to the formation of a shell having enhanced imperviousness. In particular, the shell shows enhanced imperviousness with respect to low-molecular weight materials, i.e. materials having a molecular weight lower than 250 g/mol, such as fragrance ingredients.

Furthermore, compared to conventional core-shell microcapsules of the above-mentioned kind, capsules obtained by the process according to the present invention show increased stability in liquid consumer product formulations, in particular water-based consumer products, such as fabric care conditioners.

Moreover, the applicant has found that by performing the aforementioned process, it is possible to better control the size of the microcapsules, compared to conventional complex coacervation. In particular, it becomes possible to obtain microcapsules in sizes below 75 µm. This is much lower than the microcapsule sizes reported in the prior art. This is also much more advantageous as it is known that microcapsules having size below 75 µm deposit better on substrates during rinse-off applications than larger microcapsules.

In preferred embodiments of the present invention, the shell can be formed by cross-linking of the at least one protein and a polyfunctional nucleophile with the first cross-linking agent. It has been found that, by addition of a polyfunctional nucleophile in the cross-linking process, the stability of the capsules in the above-mentioned liquid consumer product formulations is further improved.

Proteins that are particularly suitable for the sake of the present invention include gelatins, whey proteins, pea proteins, soy proteins, caseins and albumins, for instance bovine serum albumin.

In preferred embodiments of the present invention, the at least one protein is a gelatin, preferably a Type B gelatin.

Type B gelatin can be obtained from the alkaline treatment of collagen and is well known for its ability to form complexes with anionic polyelectrolytes, such as negatively charged polysaccharides under mild acidic conditions.

Gelatin is usually characterized by so-called "Bloom Strength". In the context of the present invention, the Bloom Strength refers to the rigidity of a gelatin film, as measured by so-called "Bloom Gelometer", according to the Official Procedures of the Gelatin Manufacturers Institute of America, Inc., revised 2019, Chapter 2.1. According to this procedure, the Bloom Strength, expressed in Bloom, is equal to the weight, expressed in g, required to move vertically a standardized plunger, having a diameter of 12.5 mm, to a depth of 4 mm into a gelatin gel, which has been prepared under controlled conditions, i.e. by dissolving 6.67 wt.-% of gelatin in deionized water at 60° C., in a standardized jar, and letting the gel form for 17 hours at 10° C. The higher the weight is, the higher is the Bloom Strength of the gelatin used for making the tested gel.

In preferred embodiments of the present invention, the Type B gelatin has a Bloom Strength of 200 to 250 Bloom.

If the Bloom Strength is too low, the gel is mechanically weak and coacervates obtained therefrom may not form a self-standing layer of gelatin-rich phase around the core composition. If the Bloom Strength is too high, then the coacervates and the gelatin-rich phase obtained therefrom may be too brittle.

In preferred embodiments of the present invention, the Type B gelatin is obtainable from fish, because fish gelatin meets better acceptance within consumer than beef or pork gelatin, mainly due to health concerns, sociological context or religious rules.

Alternatively, the protein may be a vegetable protein, in particular a pea protein and/or a soy protein, which have the advantage of being vegan.

In preferred embodiments of the present invention, the first cross-linking agent is a trifunctional araliphatic isocyanate.

Without being bound by any theory, the applicant believes that araliphatic isocyanate groups have the advantage of possessing an intermediate reactivity compared to the highly reactive aromatic isocyanates and the less reactive aliphatic isocyanate.

More preferably, the trifunctional araliphatic isocyanate is an adduct of 2-ethylpropane-1,2,3-triol or 2-ethyl-2-(hydroxymethyl)propane-1,3-diol with 1-isocyanato-2-(isocyanatomethyl)benzene, 1-isocyanato-3-(isocyanatomethyl)benzene and/or 1-isocyanato-4-(isocyanatomethyl)-benzene.

In a particularly preferred embodiment, the trifunctional araliphatic isocyanate is an adduct of 2-ethylpropane-1,2,3-triol with 1-isocyanato-3-(isocyanatomethyl)benzene.

Adducts of 2-ethylpropane-1,2,3-triol with 1-isocyanato-3-(isocyanatomethyl)benzene are available commercially under the trade names Takenate D110-N (ex Mitsui Chemicals) or Quix 175 (ex Covestro).

The polyfunctional nucleophile can be selected from the group consisting of polyamines, in particular diamines and triamines, polyols, ureas, urethanes and thiols.

In particular, the polyfunctional nucleophile can be selected from the group consisting of ethylenediamine, diethylenetriamine, triethylenetetramine, tetraethylenepentamine, pentaethylenehexamine, 1,3-diaminopropane, 1,2-diaminopropane, 1,4-diaminobutane, 1,6-diaminohexane, bis(3-aminopropyl)amine, bis(hexanethylene)triamine, tris (2-aminoethyl)amine, N,N'-bis(3-aminopropyl)-1,3-propanediamine, chitosan, nisin, arginine, lysine, ornithine, biuret, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine, 2,2'-ethylenedioxy)bis (ethylamine) and 4,7,10-trioxa-1,13-tridecanediamineresorcinol.

Furthermore, the polyfunctional nucleophile can be selected from the group consisting of guanidine, guanidine salts (for instance guanidine carbonate or guanidine hydrochloride), 1,3-diamino-guanidine, 1,1-dimethylbiguanide and 2,4,6-triaminopyrimidineguanazol.

The polyfunctional nucleophile can also be an aromatic polyamine, preferably an arylalkylamine, such as m-xylylenediamine or p-xylylenediamine.

Furthermore, the polyfunctional nucleophile can also be a cycloaliphatic diamine, such as 4,4'-diaminodicyclohexylmethane, 1,4-cyclohexanebismethylamine, isophorone diamine or 1,4-diazacycloheptane.

Moreover, the polyfunctional nucleophile can be selected from polyols, such as polyphenols and polysaccharides, in particular pentaerythritol, dipentaerythritol, glycerol, polyglycerol, ethylene glycol, polyethylene glycol, trimethylolpropane, neopentyl glycol, sorbitol, erythritol, threitol, arabitol, xylitol, ribitol, mannitol, galactitol, fucitol, iditol, inositol, volemitol, isomalt, maltitol, lactitol, maltotriitol, maltotetraitol, polyglycitol, polyphenol and tannic acid.

In preferred embodiments of the present invention, the polyfunctional nucleophile is selected from the group consisting of melamine and urea.

Preferably, the polyfunctional nucleophile is water-soluble.

In preferred embodiments of the present invention, the weight ratio of the polyfunctional nucleophile, in particular the melamine, to the at least one protein, in particular the gelatin, is from 0.01 to 1.0, preferably from 0.05 to 0.5, more preferably from 0.08 to 0.2, even more preferably from 0.1 to 0.15.

In preferred embodiments of the present invention, the at least one polysaccharide comprises carboxylic acid groups. Polysaccharides comprising carboxylic acid groups are particularly suitable for complex coacervation with proteins, in particular with Type B gelatin. This is due to the fact that the net electrical charge of these polysaccharides may be adjusted by adjusting the pH, so that the complexation with ampholytic proteins is facilitated. Complexation occurs at the pH where the protein has an overall positive electrical charge, whereas the polysaccharide as an overall negative charge, so that the overall electrical charge of the complex is neutral. These polysaccharides include native polysaccharides from nature and modified polysaccharides. Monovalent alkaline metal salts of these polysaccharides may also be used.

In particular, the at least one polysaccharide is selected from the group consisting of carboxymethylcellulose, gum Arabic, alginate, pectin, hyaluronic acid, xanthan gum, gellan gum, and their salts with monovalent alkaline metals. Carboxymethylcellulose, sodium carboxymethylcellulose and gum Arabic are particularly preferred.

Among the two variants of gum Arabic, i.e. gum acacia Senegal and gum acacia Seyal, gum acacia Senegal is preferred, owing to the higher level of glucuronic acid in gum acacia Senegal.

The at least one polysaccharide can be selected from the group consisting of carboxymethylcellulose and sodium carboxymethylcellulose, wherein the carboxymethylcellulose and/or the sodium carboxymethylcellulose have a molecular weight of from 50,000 to 250,000 g/mol, preferably from 75,000 to 125,000 g/mol and a degree of substitution of from 0.5 to 1.0, preferably from 0.6 to 0.8.

In preferred embodiments of the present invention, the imperviousness and stability of the shell may be further improved by cross-linking of the complex coacervate with a second cross-linking agent.

In particularly preferred embodiments, the second cross-linking agent is a difunctional aldehyde selected from the group consisting of succinaldehyde, glutaraldehyde, glyoxal, benzene-1,2-dialdehyde, benzene-1,3-dialdehyde, benzene-1,4-dialdehyde, piperazine-N,N-dialdehyde, and 2,2'-bipyridyl-5,5'-dialdehyde. Di-functional aldehydes are known to be effective cross-linking agents for proteins.

In preferred embodiments, the process according to the present invention comprises the steps of:

a) Providing a core composition comprising the first cross-linking agent;

b) Providing an aqueous phase comprising the at least one protein and optionally a polyfunctional nucleophile;

c) Optionally: Heating the aqueous phase in order to dissolve the at least one protein and further optionally the polyfunctional nucleophile;

d) Emulsifying the core composition provided in step a) in the aqueous phase provided in step b) or step c) in order to obtain core composition droplets having a volume median size of 1 to 100 μm, preferably 5 to 75 μm, more preferably 8 to 60 μm even more preferably 10 to 25 μm or 35 to 55 μm, dispersed in the aqueous phase;

e) Heating the emulsion obtained in step d), preferably to a temperature of at least 60° C., more preferably at least 80° C., even more preferably at least 90° C., in particular for at least 10 minutes;

f) Letting the emulsion obtained in step e) cool, preferably to a temperature from 25 to 35° C., more preferably from 30 to 32° C., in particular in order to form the simple coacervate;

g) Adding an aqueous solution of the polysaccharide to the mixture formed in step f);

h) Adjusting the pH of the mixture formed in step g) in order to induce formation of the complex coacervate;

i) Optionally: Letting the slurry obtained in step h) cool, preferably to a temperature of 10 to 15° C.;

j) Optionally: Adding the second cross-linking agent and maintaining the mixture under stirring while letting it warm up to room temperature;

k) Obtaining the plurality of core-shell microcapsules.

The microcapsules obtained by the process according to the present invention exhibit significantly better properties in terms of microcapsule size, storage stability and olfactive performance than microcapsules obtained by conventional coacervation processes.

In preferred embodiments of the present invention, the weight ratio of the first cross-linking agent, in particular the trifunctional araliphatic isocyanate, to the at least one protein, in particular the gelatin, is from 0.08 to 1.2, preferably from 0.12 to 0.8, more preferably from 0.16 to 0.6, even more preferably from 0.2 to 0.4.

With such weight ratios of first cross-linking agent to protein, good stability of the microcapsules, in particular with respect to leakage, can be achieved while at the same time ensuring biodegradability. In context of the present invention biodegradability is particularly measured according to OECD method 301F. In preferred embodiments of the present invention, the percentage of degradation measured with this method is at least 50 wt.-%, preferably at least 55 wt.-%, more preferably at least 60 wt.-%, even more preferably at least 65 wt.-%, still more preferably at least 70 wt.-%, even still more preferably at least 75 wt.-%. In the present context, the weight ratio of the first cross-linking agent to the at least one protein is in particular based on the amount of active first cross-linking agent.

In preferred embodiments of the present invention, the volume median diameter Dv(50) of the plurality of core-shell microcapsules is from 1 to 100 μm, preferably 5 to 75 μm, more preferably 8 to 60 μm, even more preferably 10 to 25 μm or 35 to 55 μm. Microcapsules having volume median diameter in the range from 8 to 60 μm show optimal deposition on various substrates, such as fabrics and hair. Moreover, in order to be sufficiently stable with respect to leakage, the trifunctional araliphatic isocyanate to protein, in particular gelatin, weight ratio is additionally preferably within the aforementioned preferred range, from 0.08 to 1.2, preferably from 0.12 to 0.8, more preferably from 0.16 to 0.6, even more preferably from 0.2 to 0.4.

The weight ratio of polysaccharide to protein typically depends on the nature of the polysaccharide. Without being bound by any theory, it is assumed that this weight ratio depends on the degree of substitution of the polysaccharide, in particular with carboxylic or carboxylate groups, if applicable.

Preferably, the weight ratio between the at least one polysaccharide and the at least one protein is from 0.05 to 0.5, preferably from 0.08 to 0.2.

In particular embodiments of the present invention, the above-described process may additionally comprise the step of adding after step h) or after step j) or after step k) a at least one suspending agent. Such suspending agents may prevent the formation of microcapsule agglomerates and/or prevent the microcapsule to cream or sediment.

Suspending agents that are particularly useful for the sake of the present invention include starch and starch derivatives, such as modified starch, dextrin, xanthan gum, gum tragacanth, gum karaya, guar gum, diutan gum; cellulose and cellulose derivatives, such as hydroxyethyl cellulose, hydroxyethyl cellulose/lauryl-dimethylammoniumepoxy condensate, hydroxypropyl-cellulose, cationic cellulose (for example Polyquaternium-4), cellulose gum; carrageenan; agar-agar; pectins and pectic acid; gelatin; protein hydrolysates; polymer and copolymers of vinyl and allyl monomers, such as polyvinylpyrrolidone; poly(vinyl pyrrolidone-co-vinyl acetate); poly(vinyl alcohol-co-vinyl acetate), more particularly hydrolyzed poly(vinyl acetates) having a degree of hydrolysis between 85 and 92%; vinyl ester homopolymers and copolymers, such as vinyl acetate, vinyl pivalate, vinyl versatate; poly(vinyl methyl ether), polymer and copolymer of vinyl alkyl amines, such as vinyl methylamine, quaternized vinyl alkyl amines, vinyl pyridine, quaternized vinyl pyridine, vinyl imidazoline, vinyl imidazole, vinyl imidazolinium, dimethyldiallyl ammonium chloride; polyamines and polyimines; ethoxylated polyamines; polymers and copolymers of (meth)acrylamides, N-alkyl-(meth)

acrylamides, such as N,N-dimethylaminoalkyl methacrylate, quaternized N-alkyl-(meth)acrylamides, such as methacrylamidopropyl-trimethylammonium chloride, acrylamide-ethyltrimmonium chloride, acrylamidolauryltrimethyl-ammonium chloride and 2-(acryloyloxy)-N,N,N-trimethylethanaminium chloride; poly(alkylene-oxide); polyurethanes and polyureas, such as cationic non-ionic and amphoteric polyurethanes and polyureas; mixed copolymers thereof; and mixture thereof.

In particular embodiments of the present invention, the process may additionally comprise the step of adding after step h) or after step j) or after step k) at least one preservative.

Suitable preservatives include quaternary compounds, biguanide compounds polyaminopropyl biguanidine, hexetidine, para-chloro-meta-cresol, methenamine, 3-bis(hydroxymethyl)-5,5-dimethylimidazolidine-2,4-dione, quaternium-15, benzoic acid, salicylic acid, undec-10-enoic acid, formic acid, biphenyl-2-ol and their salts, 4-hydroxybenzoic acid and its esters and salts; sorbic acid and its salts, isothiazolinones, bronopol (2-bromo-2-nitro-1,3-propanediol), 5-bromo-5-nitro-1,3-dioxane, thiabendazone, benzimidazole carbamate, triclocarban; 3-iodo-2-propynylbutyl-carbamate, thiomersal; triclosan, dichlorobenzyl alcohol, chloroxylenol, imidazolidinyl urea, phenoxyethanol, benzyl alcohol; caprilyl glycol and mixture thereof.

In preferred embodiments of the present invention, the core or the core composition, respectively, comprises at least one functional material, in particular selected from the group consisting of fragrance ingredients, cosmetic ingredients and biologically active ingredients.

The at least one functional material is typically hydrophobic or has a limited solubility in water, for example less than 2.5 g per 100 g of water, preferably less than 1 g per 100 g of water, still more preferably less than 0.1 g per 100 g of water. Preferably, the at least one functional material is liquid or soluble in apolar solvents, such as oils. Preferably, the at least one functional material has a calculated octanol/water partition coefficient (ClogP) of 1.5 or more, more preferably 2 or more. Preferably, the ClogP of the at least one functional cosmetic ingredients is from about 2 to about 7.

In preferred embodiments of the present invention, the core composition comprises at least one fragrance ingredient. A comprehensive list of fragrance ingredients that may be encapsulated in accordance with the present invention may be found in the perfumery literature, for example "Perfume & Flavor Chemicals", S. Arctander (Allured Publishing, 1994). Encapsulated perfumes according to the present invention preferably comprise fragrance ingredients selected from ADOXAL (2,6,10-trimethylundec-9-enal); AGRUMEX (2-(tert-butyl)cyclohexyl acetate); ALDEHYDE C 10 DECYLIC (decanal); ALDEHYDE C 11 MOA (2-methyldecanal); ALDEHYDE C 11 UNDECYLENIC (undec-10-enal); ALDEHYDE C 110 UNDECYLIC (undecanal); ALDEHYDE C 12 LAURIC (dodecanal); ALDEHYDE C 12 MNA PURE (2-methylundecanal); ALDEHYDE ISO C 11 ((E)-undec-9-enal); ALDEHYDE MANDARINE 10%/TEC ((E)-dodec-2-enal); ALLYL AMYL GLYCOLATE (allyl 2-(isopentyloxy)acetate); ALLYL CYCLOHEXYL PROPIONATE (allyl 3-cyclohexylpropanoate); ALLYL OENANTHATE (allyl heptanoate); AMBER CORE (1-((2-(tert-butyl)cyclohexyl)oxy)butan-2-ol); AMBERMAX (1,3,4,5,6,7-hexahydro-.beta.,1,1,5,5-pentamethyl-2H-2,4a-Methanonaphthalene-8-ethanol); AMYL SALICYLATE (pentyl 2-hydroxybenzoate); APHERMATE (1-(3,3-dimethylcyclohexyl)ethyl formate);

BELAMBRE ((1R,2S,4R)-2'-isopropyl-1,7,7-trimethylspiro[bicyclo[2.2.1]heptane-2,4'-[1,3]dioxane]); BIGARYL (8-(sec-butyl)-5,6,7,8-tetrahydroquinoline); BOISAMBRENE FORTE ((ethoxymethoxy)-cyclododecane); BOISIRIS ((1S,2R,5R)-2-ethoxy-2,6,6-trimethyl-9-methylene-bicyclo [3.3.1]nonane); BORNYL ACETATE ((2S,4S)-1,7,7-trimethylbicyclo[2.2.1]-heptan-2-yl acetate); BUTYL BUTYRO LACTATE (1-butoxy-1-oxopropan-2-yl butyrate); BUTYL CYCLOHEXYL ACETATE PARA (4-(tert-butyl)cyclohexyl acetate); CARYOPHYLLENE ((Z)-4,11,11-trimethyl-8-methylenebicyclo[7.2.0]-undec-4-ene); CASHMERAN (1,1,2,3,3-pentamethyl-2,3,6,7-tetrahydro-1H-inden-4(5H)-one); CASSYRANE (5-tert-butyl-2-methyl-5-propyl-2H-furan); CITRAL ((E)-3,7-dimethylocta-2,6-dienal); CITRAL LEMAROME N ((E)-3,7-dimethylocta-2,6-dienal); CITRATHAL R ((Z)-1,1-diethoxy-3,7-dimethylocta-2,6-diene); CITRONELLAL (3,7-dimethyloct-6-enal); CITRONELLOL (3,7-dimethyloct-6-en-1-ol); CITRONELLYL ACETATE (3,7-dimethyloct-6-en-1-yl acetate); CITRONELLYL FORMATE (3,7-dimethyloct-6-en-1-yl formate); CITRONELLYL NITRILE (3,7-dimethyloct-6-enenitrile); CITRONELLYL PROPIONATE (3,7-dimethyloct-6-en-1-yl propionate); CLONAL (dodecanenitrile); CORANOL (4-cyclohexyl-2-methylbutan-2-ol); COSMONE ((Z)-3-methylcyclotetradec-5-enone); CYCLAMEN ALDEHYDE (3-(4-isopropylphenyl)-2-methylpropanal); CYCLOGALBANATE (allyl 2-(cyclohexyloxy)acetate); CYCLOHEXYL SALICYLATE (cyclohexyl 2-hydroxybenzoate); CYCLOMYRAL (8,8-dimethyl-1,2,3,4,5,6,7,8-octahydronaphthalene-2-carbaldehyde); DAMASCENONE ((E)-1-(2,6,6-trimethylcyclohexa-1,3-dien-1-yl)but-2-en-1-one); DAMASCONE ALPHA ((E)-1-(2,6,6-trimethylcyclohex-2-en-1-yl)but-2-en-1-one); DAMASCONE DELTA ((E)-1-(2,6,6-trimethylcyclohex-3-en-1-yl)but-2-en-1-one); DECENAL-4-TRANS ((E)-dec-4-enal); DELPHONE (2-pentylcyclopentanone); DIHYDRO ANETHOLE (propanedioic acid 1-(1-(3,3-dimethylcyclohexyl)ethyl) 3-ethyl ester); DIHYDRO JASMONE (3-methyl-2-pentylcyclopent-2-enone); DIMETHYL BENZYL CARBINOL (2-methyl-1-phenylpropan-2-ol); DIMETHYL BENZYL CARBINYL ACETATE (2-methyl-1-phenylpropan-2-yl acetate); DIMETHYL BENZYL CARBINYL BUTYRATE (2-methyl-1-phenylpropan-2-yl butyrate); DIMETHYL OCTENONE (4,7-dimethyloct-6-en-3-one); DIMETOL (2,6-dimethylheptan-2-ol); DIPENTENE (1-methyl-4-(prop-1-en-2-yl)cyclohex-1-ene); DUPICAL ((E)-4-((3aS,7aS)-hexahydro-1H-4,7-methanoinden-5(6H)-ylidene)butanal); EBANOL ((E)-3-methyl-5-(2,2,3-trimethylcyclopent-3-en-1-yl)pent-4-en-2-ol); ETHYL CAPROATE (ethyl hexanoate); ETHYL CAPRYLATE (ethyl octanoate); ETHYL LINALOOL ((E)-3,7-dimethylnona-1,6-dien-3-ol); ETHYL LINALYL ACETATE ((Z)-3,7-dimethylnona-1,6-dien-3-yl acetate); ETHYL OENANTHATE (ethyl heptanoate); ETHYL SAFRANATE (ethyl 2,6,6-trimethylcyclohexa-1,3-diene-1-carboxylate); EUCALYPTOL ((1s,4s)-1,3,3-trimethyl-2-oxabicyclo[2.2.2]octane); FENCHYL ACETATE ((2S)-1,3,3-trimethylbicyclo[2.2.1]heptan-2-yl acetate); FENCHYL ALCOHOL ((1S,2R,4R)-1,3,3-trimethylbicyclo[2.2.1]heptan-2-ol); FIXOLIDE (1-(3,5,5,6,8,8-hexamethyl-5,6,7,8-tetrahydronaphthalen-2-yl)ethanone); FLOR-ALOZONE (3-(4-ethylphenyl)-2,2-dimethylpropanal); FLORHYDRAL (3-(3-isopropylphenyl)butanal); FLOROCYCLENE ((3aR,6S,7aS)-3a,4,5,6,7,7a-hexahydro-1H-4,7-methanoinden-6-yl propionate); FLOROPAL (2,4,6-trimethyl-4-phenyl-1,3-dioxane); FRESKOMENTHE (2-(sec-butyl)cyclohexanone); FRUITATE ((3aS,4S,7R,7aS)-ethyl octahydro-1H-4,7-methanoindene-3a-carboxylate); FRUTONILE (2-methyldecanenitrile); GALBANONE PURE (1-(3,3-dimethylcyclohex-1-en-1-yl)pent-4-en-1-one); GARDOCYCLENE ((3aR,6S,7aS)-3a,4,5,6,7,7a-hexahydro-1H-4,7-methanoinden-6-yl isobutyrate); GERANIOL ((E)-3,7-dimethylocta-2,6-dien-1-ol); GERANYL ACETATE SYNTHETIC ((E)-3,7-dimethylocta-2,6-dien-1-yl acetate); GERANYL ISOBUTYRATE ((E)-3,7-dimethylocta-2,6-dien-1-yl isobutyrate); GIVESCONE (ethyl 2-ethyl-6,6-dimethylcyclohex-2-enecarboxylate); HABANOLIDE ((E)-oxacyclohexadec-12-en-2-one); HEDIONE (methyl 3-oxo-2-pentylcyclopentaneacetate); HERBANATE ((2S)-ethyl 3-isopropylbicyclo[2.2.1]hept-5-ene-2-carboxylate); HEXENYL-3-CIS BUTYRATE ((Z)-hex-3-en-1-yl butyrate); HEXYL CINNAMIC ALDEHYDE ((E)-2-benzylideneoctanal); HEXYL ISOBUTYRATE (hexyl isobutyrate); HEXYL SALICYLATE (hexyl 2-hydroxybenzoate); INDOFLOR (4,4a,5,9b-tetrahydroindeno[1,2-d][1,3]dioxine); IONONE BETA ((E)-4-(2,6,6-trimethylcyclohex-1-en-1-yl)but-3-en-2-one); IRISONE ALPHA ((E)-4-(2,6,6-trimethylcyclohex-2-en-1-yl)but-3-en-2-one); IRONE ALPHA ((E)-4-(2,5,6,6-tetramethylcyclohex-2-en-1-yl)but-3-en-2-one); ISO E SUPER (1-(2,3,8,8-tetramethyl-1,2,3,4,5,6,7,8-octahydronaphthalen-2-yl)ethanone); ISOCYCLO-CITRAL (2,4,6-trimethylcyclohex-3-enecarbaldehyde); ISONONYL ACETATE (3,5,5-trimethylhexyl acetate); ISOPROPYL METHYL-2-BUTYRATE (isopropyl 2-methyl butanoate); ISORALDEINE 70 ((E)-3-methyl-4-(2,6,6-trimethylcyclohex-2-en-1-yl)but-3-en-2-one); JASMACYCLENE ((3aR,6S,7aS)-3a,4,5,6,7,7a-hexahydro-1H-4,7-methanoinden-6-yl acetate); JASMONE CIS ((Z)-3-methyl-2-(pent-2-en-1-yl)cyclopent-2-enone); KARANAL (5-(sec-butyl)-2-(2,4-dimethylcyclohex-3-en-1-yl)-5-methyl-1,3-dioxane); KOAVONE ((Z)-3,4,5,6,6-pentamethylhept-3-en-2-one); LEAF ACETAL ((Z)-1-(1-ethoxyethoxy)hex-3-ene); LEMONILE ((2E,6Z)-3,7-dimethylnona-2,6-dienenitrile); LIFFAROME GIV ((Z)-hex-3-en-1-yl methyl carbonate); LILIAL (3-(4-(tert-butyl)phenyl)-2-methylpropanal); LINALOOL (3,7-dimethylocta-1,6-dien-3-ol); LINALYL ACETATE (3,7-dimethylocta-1,6-dien-3-yl acetate); MAHONIAL ((4E)-9-hydroxy-5,9-dimethyl-4-decenal); MALTYL ISOBUTYRATE (2-methyl-4-oxo-4H-pyran-3-yl isobutyrate); MANZANATE (ethyl 2-methylpentanoate); MELONAL (2,6-dimethylhept-5-enal); MENTHOL (2-isopropyl-5-methylcyclohexanol); MENTHONE (2-isopropyl-5-methylcyclohexanone); METHYL CEDRYL KETONE (1-((1S,8aS)-1,4,4,6-tetramethyl-2,3,3a,4,5,8-hexahydro-1H-5,8a-methanoazulen-7-yl)ethanone); METHYL NONYL KETONE EXTRA (undecan-2-one); METHYL OCTYNE CARBONATE (methyl non-2-ynoate); METHYL PAMPLEMOUSSE (6,6-dimethoxy-2,5,5-trimethylhex-2-ene); MYRALDENE (4-(4-methylpent-3-en-1-yl)cyclohex-3-enecarbaldehyde); NECTARYL (2-(2-(4-methylcyclohex-3-en-1-yl)propyl)cyclopentanone); NEOBERGAMATE FORTE (2-methyl-6-methyleneoct-7-en-2-yl acetate); NEOFOLIONE ((E)-methyl non-2-enoate); NEROLIDYLE ((Z)-3,7,11-trimethyldodeca-1,6,10-trien-3-yl acetate); NERYL ACETATE HC ((Z)-3,7-dimethylocta-2,6-dien-1-yl acetate); NONADYL (6,8-dimethylnonan-2-ol); NONENAL-6-CIS ((Z)-non-6-enal); NYMPHEAL (3-(4-isobutyl-2-methylphenyl)propanal); ORIVONE (4-(tert-pentyl)cyclohexanone); PARADISAMIDE (2-ethyl-N-methyl-N-(m-tolyl)butanamide); PELARGENE (2-methyl-4-methylene-6-phenyltetrahydro-2H-pyran); PEONILE (2-cyclohexylidene-2-phenylacetonitrile); PETALIA (2-cyclohexylidene-2-(o-tolyl)acetonitrile); PIVAROSE (2,2-dimethyl-2-pheylethyl propanoate); PRECYCLEMONE B (1-methyl-4-(4-methylpent-3-en-1-yl)cyclohex-3-enecarb-aldehyde); PYRALONE (6-(sec-butyl)quinoline); RADJA-NOL SUPER ((E)-2-ethyl-4-(2,2,3-trimethylcyclopent-3-en-1-yl)but-2-en-1-ol); RASPBERRY KETONE (N112) (4-(4-hydroxyphenyl)butan-2-one); RHUBAFURANE (2,2,5-trimethyl-5-pentylcyclopentanone); ROSACETOL (2,2,2-trichloro-1-phenylethyl acetate); ROSALVA (dec-9-en-1-ol); ROSYFOLIA ((1-methyl-2-(5-methylhex-4-en-2-yl)cyclopropyl)-methanol); ROSYRANE SUPER (4-methylene-2-phenyltetrahydro-2H-pyran); SERENO-LIDE (2-(1-(3,3-dimethylcyclohexyl)-ethoxy)-2-methylpro-pyl cyclopropanecarboxylate); SILVIAL (3-(4-isobutylphe-nyl)-2-methylpropanal); SPIROGALBANONE (1-(spiro[4.5]dec-6-en-7-yl)pent-4-en-1-one); STEMONE ((E)-5-methylheptan-3-one oxime); SUPER MUGUET ((E)-6-ethyl-3-methyloct-6-en-1-ol); SYLKOLIDE ((E)-2-((3,5-dimethylhex-3-en-2-yl)oxy)-2-methylpropyl cyclopropanecarboxylate); TERPINENE GAMMA (1-methyl-4-propan-2-ylcyclohexa-1,4-diene); TERPI-NOLENE (1-methyl-4-(propan-2-ylidene)cyclohex-1-ene); TERPINYL ACETATE (2-(4-methylcyclohex-3-en-1-yl)propan-2-yl acetate); TETRAHYDRO LINALOOL (3,7-dimethyloctan-3-ol); TETRAHYDRO MYRCENOL (2,6-dimethyloctan-2-ol); THIBETOLIDE (oxacyclohexadecan-2-one); TRIDECENE-2-NITRILE ((E)-tridec-2-enenitrile); UNDECAVERTOL ((E)-4-methyldec-3-en-5-ol); VELOU-TONE (2,2,5-trimethyl-5-pentylcyclopentanone); VIRI-DINE ((2,2-dimethoxyethyl)benzene); ZINARINE (2-(2,4-dimethylcyclohexyl)pyridine).

The core composition may also comprise at least one fragrance precursor, meaning a material that is capable of releasing a fragrance ingredient by the means of a stimulus, such as a change of temperature, the presence of oxidants, the action of enzymes or the action of light. Such fragrance precursors are well-known to the art.

The core composition may also comprise at least one functional cosmetic ingredient. The functional cosmetic ingredients for use in the encapsulated composition are preferably hydrophobic.

Particularly useful functional cosmetic ingredients may be selected from the group consisting of emollients, smoothening ingredients, hydrating ingredients, soothing and relaxing ingredients, decorative ingredients, deodorants, anti-aging ingredients, cell rejuvenating ingredients, draining ingredients, remodeling ingredients, skin levelling ingredients, preservatives, anti-oxidants, antibacterial or bacteriostatic ingredients, cleansing ingredients, lubricating ingredients, structuring ingredients, hair conditioning ingredients, whitening ingredients, texturing ingredients, softening ingredients, anti-dandruff ingredients, and exfoliating ingredients.

Particularly useful functional cosmetic ingredients include, but are not limited to hydrophobic polymers, such as alkyldimethylsiloxanes, polymethylsil-sesquioxanes, polyethylene, polyisobutylene, styrene-ethylene-styrene and styrene-butylene-styrene block copolymers, and the like; mineral oils, such as hydrogenated isoparaffins, silicone oils and the like; vegetable oils, such as argan oil, jojoba oil, aloe vera oil, and the like; fatty acids and fatty alcohols and their esters; glycolipides; phospholipides; sphingolipides, such as ceramides; sterols and steroids; terpenes, sesquiterpenes, triterpenes and their derivatives; essential oils, such as *Arnica* oil, *Artemisia* oil, Bark tree oil, Birch leaf oil, Calendula oil, Cinnamon oil, *Echinacea* oil, *Eucalyptus* oil, *Ginseng* oil, Jujube oil, *Helianthus* oil, Jasmine oil, Lavender oil, Lotus seed oil, *Perilla* oil, Rosmary oil, Sandal wood oil, Tea tree oil, Thyme oil, Valerian oil, Wormwood oil, Ylang Ylang oil, and *Yucca* oil.

In particular, the at least one functional cosmetic ingredient may be selected from the group consisting of Sandal wood oil, such as Fusanus Spicatus kernel oil; Panthenyl triacetate; Tocopheryl acetate; Tocopherol; Naringinin; Ethyl linoleate; Farnesyl acetate; Farnesol; Citronellyl methyl crotonate; and Ceramide-2 (1-Stearoiyl-C18-Sphingosine, CAS-No: 100403-19-8).

The process according to the present invention may also comprise the step of drying the microcapsules.

Optionally, additional materials may be added to the powder, such as carrier materials, such as salts, silicates, clays and carbohydrates, fire proofing materials, additional functional materials, such as fragrance ingredients, cosmetic ingredients, biologically active ingredients, and substrate enhancers, additional encapsulating materials, such as polysaccharides, proteins, alkoxysilanes, synthetic polymers and copolymers, surfactants and waxes.

Drying methods such as spray-drying, spray-coating, belt and drum drying may be employed. These methods are well known to the art.

In particular, the drying process may be accompanied by an additional encapsulation process, wherein an additional functional material is entrapped in an additional encapsulating material. For example, the slurry to be dried may comprise, additionally to the core-shell microcapsules obtained in the process according to the present invention, at least one non-encapsulated functional material and at least one water-soluble encapsulating material, so that the functional material, that is not encapsulated in the core-shell microcapsule, is entrapped in the water-soluble encapsulating material during drying. Typically, the at least one water-soluble encapsulating material comprises at least one hydrocolloid, such as starch octenyl succinate and gum acacia. The hydrocolloid promotes and stabilizes the dispersion of the non-encapsulated material in the aqueous phase of the slurry, so that, upon drying, a matrix is formed around or coexisting with the core-shell microcapsules.

The functional material that is encapsulated in the core-shell microcapsules may comprise a first fragrance, whereas the functional material entrapped in the water-soluble encapsulating material may comprise a second fragrance, wherein the first and second fragrances are identical or different.

Combining at least two encapsulation processes has the advantage of providing different mechanisms for releasing the functional material, for example a combination of moisture-induced and mechanical stress-induced releases.

The drying step may also be accompanied or followed by mechanical or thermal treatment, such as spheronization, granulation and extrusion.

In a second aspect, the present invention relates to an encapsulated composition obtainable by a process as described herein above.

The encapsulated composition may be in the form of liquid slurries, powder, granulates, flakes or extrudates. The composition may be used as such, for example as fragrance booster, or in diluted form in a product.

Encapsulated compositions in the form of liquid slurries may comprise from 10 to 50 wt.-%, more particularly from 15 to 25 wt.-%, of core-shell microcapsules.

Encapsulated compositions in solid form may comprise from 1 to 100 wt.-% of core-shell microcapsules. However, depending on the application or on the nature of the functional material, it may be preferable to limit or, on the contrary, to maximize the level of core-shell microcapsules in the solid form. For example, a limitation of the level of the core-shell microcapsules in the solid may be particularly desired if the encapsulated material is flammable, reactive, pungent or expensive.

Hence, the optimal level of encapsulated fragrance ingredients in a solid composition may be less than 50 wt.-%, more particularly less than 35 wt.-% and still more particularly less than 20 wt.-%, or even less than 15 wt.-%, depending on the flammability of such fragrance ingredients and the associated explosion risks.

The encapsulated fragrance may be diluted in a carrier material mentioned herein above.

The present invention also relates to a consumer product comprising an encapsulated composition as described herein above, preferably a fabric care product, a home care product or a personal care product.

The encapsulated compositions of the present invention that comprise fragrance ingredients may be used to perfume all manners of consumer products, including laundry care detergents, laundry care conditioners, fabric refreshers, personal care cleansing compositions, such as shampoos, bath and shower gels, liquid soaps, soap bars, personal care conditioning composition, such as hair care conditioners, bath and shower lotions, deodorant compositions, antiperspirant compositions, home care compositions, such as hard surface cleaners, and heavy duty detergents.

The consumer products according to the present invention may be used for treating substrates, such as fabrics, skin, hair, animate and inanimate surfaces, hard surfaces, wherein the action of treating a substrate includes washing, cleansing, softening, caring, finishing, scenting and/or deodorizing this substrate.

In one aspect of the present invention, a consumer product contains the compositions as described herein above, preferably at a level of 0.005 to 5 wt.-%, more preferably from 0.01 to 1 wt.-%, and still more preferably from 0.02 to 0.5 wt.-%, of the consumer product.

In many cases, the consumer products concerned by the present invention contain surfactants, such as anionic, cationic, amphoteric or non-ionic surfactants.

The consumer products concerned by the present invention may contain acids or bases, or substances providing acidity or alkalinity, also referred to as acidity sources or alkalinity sources.

The consumer products concerned by the present invention may contain builders for reducing water hardness, such as phosphates, polyphosphates, polycarboxylates, sodium citrate, sodium carbonate, sodium silicate, sodium aluminosilicate (zeolite).

In many cases, the consumer products concerned by the present invention are liquid and may contain further additives, such as solvents, fillers, texturing agents, such as thickener and rheological aids, distributing aids, anti-redeposition agents, preservative agents, deodorizing agents, cosmetic ingredients, and surface enhancing agents.

The consumer product containing microcapsules of the present invention may contain at least one solvent selected from water-soluble solvents, or water-insoluble, or partially water-soluble solvents.

The consumer product containing microcapsules of the present invention may contain at least one texturing agent and/or colloid stabilizer, selected from rheology modifiers, thickener, gel-forming agents, thixotropic agents, and dispersing agents.

The consumer product containing microcapsules of the present invention may contain at least one silicone, selected from, but not limited to dimethicone, poly(dimethylsiloxabedimethylsiloxane), amino-silicone, such as amodimethicone, trialkylammonium-silicone salts, ethoxylated silicones.

The consumer product containing microcapsules of the present invention may contain at least one cosmetic ingredient selected from, but not limited to emollients, moisturizing agents, anti-wrinkle agents, exfoliating agents, sunscreen agents, dyes, pigments, talcum, conditioning agents, hair styling agents, and antidandruff agents.

The consumer product containing microcapsules of the present invention may contain at least one fabric enhancing agent, selected from, but not limited to softening agents, optical brighteners and antistatic agents.

In a third aspect, the invention relates to the use of the encapsulated composition as described herein above for obtaining a consumer product.

Further features and particular advantages of the present invention become apparent from the following examples.

EXAMPLE 1: PREPARATION OF MICROCAPSULES

In Examples 1.1 to 1.5, microcapsules were prepared by performing the steps of:
- a) Providing a core composition by dissolving a known (see Table 1) amount of trifunctional araliphatic isocyanate (Takenate N100-D, ex Mitsui Inc., 75 wt.-% active content) in 165 g of a fragrance composition;
- b) Providing an aqueous phase by admixing 17 g of Type B gelatin and 150 g of deionized water;
- c) Heating up the aqueous phase to 35° C. under stirring, in order to dissolve the gelatin;
- d) Emulsifying the core composition in the aqueous phase obtained in step c) at a stirring rate of 1000 rpm, in order to obtain an emulsion of core composition droplets having a volume median diameter Dv(50) of 50 μm, dispersed in water;
- e) Heating the emulsion obtained in step d) to a temperature of 90° C. and maintaining the emulsion at this temperature for 10 min;
- f) Letting the slurry obtained in step e) cool down to a temperature of 31° C., in order to induce the simple coacervation of the cross-linked gelatin at the core-water-interface, forming thereby a slurry of core-shell microcapsules;
- g) Adding 80 g of a 2 wt.-% aqueous solution of carboxymethylcellulose in deionized water and then 534 g of deionized water to the slurry formed in step f), while maintaining the stirring rate at 1000 rpm;
- h) Adjusting the pH of the slurry to a value of 5.3 with a 10 wt.-% solution of citric acid in water; while reducing the stirring speed to 600 rpm, in order to form a cross-linked gelatin/polysaccharide coacervate at the surface of the microcapsules obtained in step f);
- i) Letting the slurry obtained in step h) cool down to a temperature of 10 to 15° C. over 1 h;
- j) Adding 0.26 g of glutaraldehyde while keeping the slurry under stirring at 15° C. for 1 min. Letting the slurry warm up to room temperature within 1 h, in order to obtain a slurry of microcapsules;
- k) Completing to 1000 g with deionized water.

The solid content of the slurry was measured by using a thermo-balance operating at 120° C. The solid content, expressed as weight percentage of the initial slurry deposited on the balance, was taken at the point where the drying-induced rate of weight change had dropped below 0.1%/min. The ratio of the measured solid content to the theoretical solid content, calculated based on the weight of fragrance composition and encapsulating materials used, was taken as a measurement of encapsulation yield, expressed in wt.-%.

The slurry was free of agglomerate, the solid content of the slurry obtained was 19 wt.-%, the volume median size Dv(50) of the capsules are reported in Table 2, and the encapsulation efficiency was 100%.

In Example 1.6, the microcapsules were produced by the same process as in Example 1.3, but carboxymethylcellulose was replaced by the same amount of gum Arabic (CAS no. 9000-01-5).

The slurry was free of agglomerate, the solid content of the slurry obtained was also 19 wt.-%, the volume median size Dv(50) of the capsules was 52 µm, and the encapsulation efficiency was 100%.

In Example 1.7, the microcapsules were obtained by the same process as in Example 1.3, but 100 g of deionized water were used in step b), instead of 150 g; and 584 g of deionized water were added in step g) instead of 534 g.

The slurry was free of agglomerate, the solid content of the slurry obtained was also 19 wt.-%, the volume median size Dv(50) of the capsules was 16 µm, and the encapsulation efficiency was 100%.

In Example 1.8, the microcapsules were obtained by the same process as in Example 1.7, but carboxymethylcellulose was replaced by the same amount of gum Arabic (CAS no. 9000-01-5).

The slurry was free of agglomerate, the solid content of the slurry obtained was also 19.5 wt.-%, the volume median size Dv(50) of the capsules was 16 µm, and the encapsulation efficiency was 100%.

In Examples 1.9 to 1.11, microcapsules were prepared by performing the steps of:

a) Providing a core composition by dissolving a known (see Table 1) amount of trifunctional araliphatic isocyanate (Takenate N100-D, ex Mitsui Inc., 75 wt.-% active content) in 250 g of a fragrance composition;

b) Providing an aqueous phase by admixing 17 g of Type B gelatin and 100 g of deionized water;

c) Heating up the aqueous phase to 35° C. under stirring, in order to dissolve the gelatin;

d) Emulsifying the core composition in the aqueous phase obtained in step c) at a stirring rate of 700 rpm, in order to obtain an emulsion of core composition droplets having a volume median diameter Dv(50) of 40-45 µm, dispersed in water;

e) Heating the emulsion obtained in step d) to a temperature of 90° C.; Maintaining the emulsion at 90° C. for 10 min, forming thereby a slurry of core-shell microcapsules;

f) Letting the slurry obtained in step e) cool down to a temperature of 31° C.;

g) When the mixture has reached ca. 50° C., adding 80 g of a 2 wt.-% aqueous solution of carboxymethylcellulose in deionized water and then 584 g of deionized water, while maintaining the stirring rate at 700 rpm;

h) Adjusting the pH of the slurry to a value of 5.4 with a 10 wt.-% solution of citric acid in water, in order to form a cross-linked gelatin/polysaccharide coacervate at the surface of the microcapsules;

i) Letting the slurry obtained in step h) cool down to a temperature of 10 to 15° C. over 1 h;

j) Adding 0.26 g of glutaraldehyde while keeping the slurry under stirring at 15° C. for 1 min. Letting the slurry warm up to room temperature within 1 h, in order to obtain a slurry of microcapsules;

k) Completing to 1000 g with deionized water.

The solid content of the slurry was 27.5 wt.-%, the volume median size Dv(50) of the capsules was 43 µm and the encapsulation efficiency was 100%.

In Example 1.10, the microcapsules were obtained by the same process as in Example 1.9, but 2 g of melamine were added in powder form to the aqueous phase after dissolution of gelatin. The solid content of the slurry was 28.0 wt.-%, the volume median size Dv(50) of the capsules was 47 µm and the encapsulation efficiency was 100%.

In Example 1.11, the microcapsules were obtained by the same process as in Example 1.10, but the 2 g of melamine were replaced by 3 g urea, which were also added in powder form to the aqueous phase after dissolution of gelatin. The solid content of the slurry was 28.1 wt.-%, the volume median size Dv(50) of the capsules was 47 µm and the encapsulation efficiency was 100%.

TABLE 1

| | Concentration of trifunctional araliphatic isocyanate and polysaccharides used | | |
| --- | --- | --- | --- |
| Example | Trifunctional isocyanate as supplied [wt.-%] | Active trifunctional isocyanate [wt.-%] | Polysaccharide |
| 1.1 | 0 | 0 | carboxymethylcellulose |
| 1.2 | 5 | 3.8 | carboxymethylcellulose |
| 1.3 | 7 | 5.3 | carboxymethylcellulose |
| 1.4 | 10 | 7.5 | carboxymethylcellulose |
| 1.5 | 14 | 10.5 | carboxymethylcellulose |
| 1.6 | 7 | 5.3 | gum Arabic |
| 1.7 | 7 | 5.3 | carboxymethylcellulose |
| 1.8 | 7 | 5.3 | gum Arabic |
| 1.9 | 10 | 7.5 | Carboxymethylcellulose |
| 1.10 | 10 | 7.5 | Carboxymethylcellulose |
| 1.11 | 10 | 7.5 | Carboxymethylcellulose |

Example 2: Comparative Examples

In comparative Example 2.1, microcapsules were obtained by applying a conventional complex coacervation process, followed by cross-linking with trifunctional araliphatic isocyanate and then with glutaraldehyde, by performing the step of:

a) Providing a core composition by dissolving 7 g of trifunctional araliphatic isocyanate (Takenate N100-D, ex Mitsui Inc., 75 wt.-% active content) in 165 g of a fragrance composition;

b) Providing an aqueous phase by admixing 17 g of type B gelatin and 150 g of deionized water;

c) Heating up the aqueous phase to 35° C. under stirring, in order to dissolve the gelatin;

d) Emulsifying the core composition in the aqueous phase mixture obtained in step c) at a stirring rate of 1000 rpm, in order to obtain an emulsion of core composition droplets dispersed in water;

e) Adding 80 g of a 2 wt.-% aqueous solution of carboxymethylcellulose in deionized water and then 534 g of deionized water to the emulsion obtained in d), while maintaining the stirring rate at 1000 rpm;

f) Letting the slurry cool down from 35° C. to a temperature of 31° C., and adjusting the pH of the slurry formed in g) to a value of 5.3 with a 10 wt.-% solution of citric acid in water; while reducing the stirring speed to 600 rpm, in order to form a gelatin/polysaccharide complex coacervate at the surface of the core composition droplets obtained in d);

g) Heating the slurry to a temperature of 90° C. and maintaining the emulsion at this temperature for 10 min, in order to obtain a slurry of microcapsules;

h) Letting the slurry obtained in step g) cool down to a temperature of 10 to 15° C.;

i) Adding 0.26 g of glutaraldehyde while keeping the slurry under stirring at this temperature for 1 min. Letting the slurry warm up to room temperature over 1 h, in order to obtain a slurry of microcapsules.

The resulting microcapsule slurry was free from agglomerates, the encapsulation efficiency was close to 100%, meaning with no visible free oil in the slurry, and the volume median size Dv(50) of the microcapsules was 400 μm. The solid content could not be measured due to the weak thermal stability of these microcapsules.

In comparative Example 2.2, microcapsules were obtained by applying a conventional complex coacervation process, followed by cross-linking with glutaraldehyde only, by performing the step of:

a) Providing a core composition consisting of 165 g of a fragrance composition;

b) Providing an aqueous phase by admixing 17 g of type B gelatin and 150 g of deionized water;

c) Heating up the aqueous phase to 35° C. under stirring, in order to dissolve the gelatin;

d) Emulsifying the core composition in the aqueous phase mixture obtained in step c) at a stirring rate of 1000 rpm, in order to obtain an emulsion of core composition droplets dispersed in water;

e) Adding 80 g of a 2 wt.-% aqueous solution of carboxymethylcellulose in deionized water and then 534 g of deionized water to the emulsion obtained in step d), while maintaining the stirring rate at 1000 rpm;

f) Letting the slurry obtained in step e) cool down from 35° C. to a temperature of 31° C., and adjusting the pH of the slurry formed in step g) to a value of 5.3 with a 10 wt.-% solution of citric acid in water; while reducing the stirring speed to 600 rpm, in order to form a gelatin/polysaccharide coacervate at the surface of the core composition droplets obtained in step d);

g) Letting the slurry obtained in step h) cool down to a temperature of 10 to 15° C.;

h) Adding 0.26 g of glutaraldehyde while keeping the slurry under stirring at this temperature for 1 min. Letting the slurry warm up to room temperature over 1 h, in order to obtain a slurry of microcapsules.

The resulting microcapsule slurry was free from agglomerates, the encapsulation efficiency was close to 100%, meaning with no visible free oil in the slurry, and the volume median size Dv(50) of the microcapsules was 250 μm. The solid content could not be measured due to the weak thermal stability of these microcapsules.

Example 3: Measurement of Fragrance Leakage in Model Extractive Medium

The model extractive medium was a system consisting of an aqueous solution of ethanol at an initial concentration of 30 vol.-% co-existing with an immiscible cyclohexane phase.

In a first step, 10 ml of cyclohexane were put into a vial. Further, 1.8 ml of a 30 vol.-% ethanol in water is added to the vial. After equilibration, taking into account the partition coefficient of ethanol between cyclohexane and water of 0.03 (see A. W. Islam, A. Zavvadi, V. N. Kabadi, Chem. Process Eng. 2012, 33, 243-253), the percentage of ethanol in the aqueous phase was 25 vol.-% and the percentage of ethanol referred to the whole system was 4.6 vol.-%.

In a second step, the slurry to be assessed was diluted in such a way that the fragrance concentration in the diluted slurry was 10 wt.-% and 200 microliters of this diluted slurry was added to the vial.

In a third step, the vial was submitted to horizontal mixing on an elliptic xy-mixing equipment operating at a 250 rpm for 4 hours (shaking in the z direction is avoided).

In a fourth step, the upper cyclohexane phase containing the extracted fragrance composition was analyzed spectrophotometrically by using a UV/visible light spectrometer. The fragrance concentration was determined by measuring the intensity of the absorbed UV/visible light at the maximum absorbance wavelength, which has been determined previously by using a reference fragrance/cyclohexane solution of known concentration. This latter reference solution was used as an external standard for the quantification of the extracted fragrance composition. The leakage value is defined as the percentage of the encapsulated fragrance composition that was recovered in the hexane phase.

Representative leakage values are given in Table 2 hereunder.

TABLE 2

| | Fragrance leakage in model extractive medium | | |
|---|---|---|---|
| Sample | Active trifunctional isocyanate [wt.-%] | Dv(50) | Leakage in wt.-% of the initial amount of encapsulated fragrance composition |
| Example 1.1 | 0 | 10 | 100 |
| Example 1.2 | 3.8 | 30 | 80 |
| Example 1.3 | 5.3 | 50 | 25 |
| Example 1.4 | 7.5 | 70 | 28 |
| Example 1.5 | 10.5 | 80 | 20 |
| Example 1.6 | 5.3 | 52 | 15 |
| Example 1.7 | 5.3 | 16 | 49 |
| Example 1.8 | 5.3 | 16 | 56 |
| Example 1.9 | 7.5 | 43 | 25 |
| Example 1.10 | 7.5 | 47 | 19 |
| Example 1.11 | 7.5 | 47 | 15 |
| Example 2.1 | 5.3 | 400 | 50 |
| Example 2.2 | 0 | 250 | 100 |

As apparent from these results, the microcapsules obtained by cross-linking gelatin with 5.3 to 10.5 wt.-% of trifunctional araliphatic isocyanate in a first step and performing a complex coacervation in a second step (Examples 1.3 to 1.6) show lower fragrance leakage than microcapsules obtained by performing a complex coacervation in a first step and cross-linking the complex is performed in a second step (Example 2.1). Microcapsules obtained by conventional gelatin/carboxymethylcellulose coacervation (Example 2.2), involving cross-linking with glutaraldehyde were not stable at all with respect to fragrance leakage in model extractive medium. The smaller microcapsules of Example 1.7 and 1.8 show higher leakage in model extractive medium, but this leakage is significantly smaller than that obtained for capsule having similar sizes, but lower trifunctional araliphatic isocyanate (Example 1.1 and 1.2). Finally, Examples 1.10 and 1.11, respectively comprising melamine and urea, show low leakage values, despite the fact that the amount of the solid content of the slurry has been increased from about 19% to about 25 wt.-%.

Example 4: Degradation Tests on Microcapsules

The core fragrance composition present in the microcapsules of Examples 1.1 to 1.7 was extracted with ethanol in an ultrasonic bath and the empty shells were washed three times with ethanol. The empty shells were then dried and submitted to a degradation test according to OECD method 301F. The results are expressed in percentage of degradation, based on the initial weight of shells submitted to the test, and reported in Table 3.

TABLE 3

| | Percentage of shell degradation according to OECD 301F method | | |
|---|---|---|---|
| Sample | Active trifunctional isocyanate [wt.-%] | Isocyanate to Gelatin Weight Ratio | Percentage of degradation [wt.-%] |
| Example 1.1 | 0 | 0 | 72 |
| Example 1.2 | 3.8 | 0.22 | 67 |
| Examples 1.3 and 1.7 | 5.3 | 0.31 | 62 |
| Example 1.4 | 7.5 | 0.44 | 58 |
| Example 1.5 | 10.5 | 0.62 | 50 |
| Example 1.6 | 5.3 | 0.31 | 65 |
| Example 1.9 | 7.5 | 0.44 | 73 |
| Example 1.10 | 7.5 | 0.44 | 58 |
| Example 1.11 | 7.5 | 0.44 | 60 |

As apparent from Table 3, increasing the concentration of trifunctional isocyanate decreases the extent of degradation. Comparing Table 2 and Table 3 shows that the optimal balance between stability and degradation is met at an active trifunctional isocyanate level of about 5 wt.-% for a slurry having a solid content of about 19 wt.-% to about 7.5 wt.-% for a slurry having a solid content of about 25 wt.-%, i.e. from about 83.3 wt.-% to about 89.3 wt.-% encapsulated fragrance composition.

Example 5: Olfactive Evaluation

The slurries of core-shell microcapsules obtained in Examples 1.3, 1.6, 1.7, 1.9, 1.10, 1.11, 2.1 and 2.2 were incorporated into a model fabric care conditioner having the composition shown in Table 4. The level of encapsulated fragrance composition was 0.19 wt.-% based on the total weight of the conditioner. The pH of the conditioner was 3.

TABLE 4

| | Conditioner composition | | |
|---|---|---|---|
| Ingredient | Supplier | INCI name | Quantity [wt.-%] |
| Calcium Chloride | VWR | Calcium chloride | 0.5 |
| Stepantex SP-90 | Stepan | Dialkylester Ammonium Methosulfate | 11.1 |
| Eumulgin CO-40 | BASF | PEG-40 Hydrogenated Castor Oil | 1 |
| Sodium benzoate | VWR | Sodium benzoate | 0.3 |
| Citric acid | VWR | Citric acid | q.s. pH 3 |
| Water | | | q.s. 99 |
| Encapsulated composition (slurry) | | | 1 |

Terry towels were submitted to a rinse cycle in a front-loaded washing machine. The amount of conditioner was 35 g for a towel load of 1 kg and the total volume of water was 20 L.

Olfactive evaluations were performed using both freshly prepared conditioner and after aging the conditioners for one month at 37° C.

For this evaluation, the terry toweling was handled carefully in order to minimize the risk of breaking the microcapsules mechanically. The pre-rub and post-rub olfactive evaluation was performed after line drying the terry toweling for 24 hours at room temperature. The olfactive performance (intensity) was assessed by a panel of 4 experts rating on a scale of 1-5 (1=barely noticeable, 2=weak, 3=medium, 4=strong and 5=very strong).

The results are reported on Table 5.

TABLE 5

| | Olfactive performance of selected encapsulated compositions in laundry care conditioner, for both fresh sample (t = 0) and aged sample (t = 1 month @ 37° C.) | | | |
|---|---|---|---|---|
| Sample | Pre-rub intensity (t = 0) | Post-rub intensity (t = 0) | Pre-rub intensity (t = 1 month @ 37° C.) | Post-rub intensity (t = 1 month @ 37° C.) |
| Example 1.3 | 2.0 | 3.5 | 2.0 | 4.0 |
| Example 1.6 | 2.5 | 4.0 | 2.0 | 3.5 |
| Example 1.7 | 2.5 | 5.0 | 2.0 | 4.0 |
| Example 1.9 | 1.5 | 4.0 | 1.2 | 3.7 |
| Example 1.10 | 1.8 | 4.3 | 1.5 | 4.0 |
| Example 1.11 | 1.0 | 3.3 | 1.1 | 3.5 |
| Example 2.1 | 4.0 | 3.0 | 1.0 | 2.0 |
| Example 2.2 | 2.0 | 1.0 | 0 | 0 |

As apparent form the results of Table 5, the microcapsules of Examples 1.3, 1.6, 1.7, and 1.9 to 1.11 perform significantly better after storage than the microcapsules of comparative Example 2.1, obtained by a conventional coacervation method, especially in terms of post-rub intensity. Microcapsules obtained by conventional coacervation (comparative Example 2.2), involving cross-linking with glutaraldehyde only, were not stable enough in the conditioner to perform significantly in fresh sample and did not perform at all after storage.

The results further show also that microcapsules of Example 1.7, even if less stable with respect to leakage in model extractive medium (Table 2), perform better than larger microcapsules, all other parameters being constant. It is surmised that the higher leakage is over-compensated by the increase of the number of microcapsules present in the system and the related higher probability of microcapsule deposition on the fabric.

The invention claimed is:

1. A process for obtaining an encapsulated composition comprising a plurality of core-shell microcapsules, wherein the core-shell microcapsules comprise a core and a shell surrounding the core, wherein the shell is formed by cross-linking of at least one protein with a first cross-linking agent, followed by the addition of at least one polysaccharide to form a complex coacervate.

2. The process according to claim 1, wherein the shell is formed by cross-linking of the at least one protein with the first cross-linking agent in order to form a simple coacervate.

3. The process according to claim 1, wherein the shell is formed by cross-linking of the at least one protein and a polyfunctional nucleophile with the first cross-linking agent.

4. The process according to claim 3, wherein the polyfunctional nucleophile is selected from the group consisting of polyamines, polyols, ureas urethanes and thiols.

5. The process according to claim 4, wherein the at least one polysaccharide is selected from the group consisting of carboxymethylcellulose, gum Arabic, alginate, pectin, hyaluronic acid, xanthan gum, gellan gum, and their salts with monovalent alkaline metals.

6. The process according to claim 1, wherein the at least one protein is a gelatin.

7. The process according to claim 6, wherein the gelatin is a Type B gelatin.

8. The process according to claim 7, wherein the Type B gelatin has a Bloom strength of 200 to 250 Bloom.

9. The process according to claim 7, wherein the Type B gelatin is obtainable from fish.

10. The process according to claim 1, wherein the first cross-linking agent is a trifunctional araliphatic isocyanate.

11. The process according to claim 10, wherein the trifunctional araliphatic isocyanate is an adduct of 2-ethyl-propane-1,2,3-triol or 2-ethyl-2-(hydroxymethyl) propane-1,3-diol with 1-isocyanato-2-(isocyanatomethyl)benzene, 1-isocyanato-3-(isocyanatomethyl)-benzene and/or 1-iso-cyanato-4-(isocyanatomethyl)benzene.

12. The process according to claim 10, wherein the trifunctional araliphatic isocyanate is an adduct of 2-ethyl-propane-1,2,3-triol with 1-isocyanato-3-(isocyanatomethyl) benzene.

13. The process according to claim 11, wherein the polyfunctional nucleophile is selected from the group consisting of melamine and urea.

14. The process according to claim 1, wherein the at least one polysaccharide comprises carboxylic acid groups.

15. The process according to claim 13, wherein the at least one polysaccharide is selected from the group consisting of carboxymethylcellulose and sodium carboxymethylcellulose, wherein the carboxymethylcellulose and/or the sodium carboxymethylcellulose have a molecular weight of from 50'000 to 250'000 g/mol and a degree of substitution of from 0.5 to 1.0.

16. The process according to claim 1, wherein the complex coacervate is cross-liked with a second cross-linking agent.

17. The process according to claim 16, wherein the second cross-linking agent is a difunctional aldehyde selected from the group consisting of succinaldehyde, glutaraldehyde, glyoxal, benzene-1,2-dialdehyde, benzene-1,3-dialdehyde, benzene-1,4-dialdehyde, piperazine-N,N-dialdehyde, and 2,2'-bipyridyl-5,5'-dialdehyde.

18. The process according to claim 16, additionally comprising the step of adding after step h) or after step j) or after step k) at least one suspending agent.

19. The process according to claim 16, additionally comprising the step of adding after step h) or after step j) or after step k) at least one preservative.

20. The process according to claim 1, comprising the steps of:

a) Providing a core composition comprising the first cross-linking agent;

b) Providing an aqueous phase comprising the at least one protein and optionally a polyfunctional nucleophile;

c) Optionally: Heating the aqueous phase in order to dissolve the at least one protein and further optionally the polyfunctional nucleophile;

d) Emulsifying the core composition provided in step a) in the aqueous phase provided in step b) or step c) in order to obtain core composition droplets having a volume median size of 1 to 100 µm, dispersed in the aqueous phase;

e) Heating the emulsion obtained in step d);

f) Letting the emulsion obtained in step e) cool;

g) Adding an aqueous solution of the polysaccharide to the mixture formed in step f);

h) Adjusting the pH of the mixture formed in step g) in order to induce formation of the complex coacervate;

i) Optionally: Letting the slurry obtained in step h) cool;

j) Optionally: Adding the second cross-linking agent and maintaining the mixture under stirring while letting it warm up to room temperature;

k) Obtaining the plurality of core-shell microcapsules.

21. The process according to claim 1, wherein the weight ratio of the first cross-linking agent to the at least one protein is from 0.08 to 1.2.

22. The process according to claim 1, wherein the volume median diameter Dv(50) of the plurality of core-shell microcapsules is from 1 to 100 µm.

23. The process according to claim 22, wherein the weight ratio between the at least one polysaccharide and the at least one protein is from 0.05 to 0.5.

24. The process according to claim 1, wherein the core or the core composition, respectively, comprises at least one functional material.

25. The process according to claim 1, wherein the core comprises at least one fragrance ingredient selected from the group consisting of 2,6,10-trimethylundec-9-enal; 2-(tert-butyl)cyclohexyl acetate; decanal; 2-methyldecanal; undec-10-enal); undecanal; dodecanal; 2-methylundecanal; (E)-undec-9-enal; (E)-dodec-2-enal; allyl 2-(isopentyloxy)acetate; allyl 3-cyclohexylpropanoate; allyl heptanoate; 1-((2-(tert-butyl)cyclohexyl)oxy)-butan-2-ol; 1,3,4,5,6,7-hexahydro-.beta., 1,1,5,5-pentamethyl-2H-2,4a-methanon-aphthalene-8-ethanol; pentyl 2-hydroxybenzoate; 1-(3,3-di-methylcyclohexyl)ethyl formate; (1R,2S,4R)-2'-isopropyl-1,7,7-trimethyl-spiro[bicyclo[2.2.1]heptane-2,4'-[1,3]dioxane]; 8-(sec-butyl)-5,6,7,8-tetra-hydroquinoline); (ethoxymethoxy)-cyclododecane; (1S,2R,5R)-2-ethoxy-2,6,6-trimethyl-9-methylene-bicyclo[3.3.1]nonane; (2S,4S)-1,7,7-trimethyl-bicyclo[2.2.1]-heptan-2-yl acetate; 1-butoxy-1-oxopropan-2-yl butyrate; 4-(tert-butyl)cyclohexyl acetate; (Z)-4,11,11-trimethyl-8-methylene-bicyclo[7.2.0]-undec-4-ene; 1,1,2,3,3-pentamethyl-2,3,6,7-tetrahydro-1H-inden-4(5H)-one; 5-tert-butyl-2-methyl-5-propyl-2H-furan; (E)-3,7-dimethylocta-2,6-dienal; (E)-3,7-dimethylocta-2,6-dienal; (Z)-1,1-diethoxy-3,7-dimethylocta-2,6-diene; 3,7-dimethyl-oct-6-enal; 3,7-dimethyloct-6-en-1-ol 3,7-dimethyloct-6-en-1-yl acetate; 3,7-dimethyloct-6-en-1-yl formate; 3,7-dimeth-yloct-6-enenitrile; 3,7-dimethyloct-6-en-1-yl propionate; dodecanenitrile; 4-cyclohexyl-2-methylbutan-2-ol; (Z)-3-methylcyclotetradec-5-enone; 3-(4-isopropylphenyl)-2-methylpropanal; (allyl 2-(cyclohexyloxy)acetate; cyclo-hexyl 2-hydroxybenzoate; 8,8-dimethyl-1,2,3,4,5,6,7,8-octahydronaphthalene-2-carbaldehyde; (E)-1-(2,6,6-trimethylcyclohexa-1,3-dien-1-yl) but-2-en-1-one; (E)-1-(2,6,6-trimethylcyclohex-2-en-1-yl) but-2-en-1-one; (E)-1-(2,6,6-trimethyl-cyclohex-3-en-1-yl) but-2-en-1-one; (E)-dec-4-enal; 2-pentylcyclopentanone; propanedioic acid 1-(1-(3,3-dimethylcyclohexyl)ethyl) 3-ethyl ester; 3-methyl-2-pentylcyclopent-2-enone; 2-methyl-1-phenylpropan-2-ol; 2-methyl-1-phenylpropan-2-yl acetate; 2-methyl-1-phenyl-propan-2-yl butyrate; 4,7-dimethyloct-6-en-3-one; 2,6-dim-ethylheptan-2-ol; 1-methyl-4-(prop-1-en-2-yl)cyclohex-1-ene; (E)-4-((3aS,7aS)-hexahydro-1H-4,7-methanoinden-5(6H)-ylidene) butanal; (E)-3-methyl-5-(2,2,3-trimethylcy-clopent-3-en-1-yl) pent-4-en-2-ol; ethyl hexanoate; ethyl octanoate; (E)-3,7-dimethylnona-1,6-dien-3-ol; (Z)-3,7-di-methylnona-1,6-dien-3-yl acetate; ethyl heptanoate; ethyl 2,6,6-trimethylcyclohexa-1,3-diene-1-carboxylate; (1s,4s)-1,3,3-trimethyl-2-oxa-bicyclo[2.2.2]octane; (2S)-1,3,3-trimethylbicyclo[2.2.1]heptan-2-yl acetate; (1S,2R,4R)-1,3,3-trimethylbicyclo[2.2.1]heptan-2-ol); 1-(3,5,5,6,8,8-hexa-methyl-5,6,7,8-tetrahydronaphthalen-2-yl) ethanone; 3-(4-ethylphenyl)-2,2-dimethylpropanal; 3-(3-isopropylphenyl) butanal; (3aR,6S,7aS)-3a,4,5,6,7,7a-hexahydro-1H-4,7- methanoinden-6-yl propionate; 2,4,6-trimethyl-4-phenyl-1,
3-dioxane; 2-(sec-butyl)cyclohexanone); (3aS,4S,7R,7aS)-
ethyl octahydro-1H-4,7-methanoindene-3a-carboxylate;
2-methyldecanenitrile; 1-(3,3-dimethylcyclohex-1-en-1-yl)
pent-4-en-1-one; (3aR,6S,7aS)-3a,4,5,6,7,7a-hexahydro-
1H-4,7-methanoinden-6-yl isobutyrate; (E)-3,7-dimethyl-
octa-2,6-dien-1-ol; (E)-3,7-dimethylocta-2,6-dien-1-yl
acetate; (E)-3,7-dimethylocta-2,6-2-one; 1-(2,3,8,8-tetram-
ethyl-1,2,3,4,5,6,7,8-octahydronaphthalen-2-yl) ethanone);
2,4,6-trimethylcyclohex-3-enecarbaldehyde; 3,5,5-dien-1-yl
isobutyrate; ethyl 2-ethyl-6,6-dimethylcyclohex-2-enecar-
boxylate; (E)-oxacyclohexadec-12-en-2-one; methyl 3-oxo-
2-pentylcyclopentaneacetate; (2S)-ethyl 3-isopropylbicyclo
[2.2.1]hept-5-ene-2-carboxylate; (Z)-hex-3-en-1-yl
butyrate; (E)-2-benzylideneoctanal; hexyl isobutyrate; hexyl
2-hydroxybenzoate; 4,4a,5,9b-tetrahydroindeno[1,2-d][1,3]
dioxine; (E)-4-(2,6,6-trimethylcyclohex-1-en-1-yl) but-3-
en-2-one; (E)-4-(2,6,6-trimethylcyclohex-2-en-1-yl) but-3-
en-2-one; (E)-4-(2,5,6,6-tetramethylcyclohex-2-en-1-yl)
but-3-en-trimethylhexyl acetate; isopropyl 2-methyl butano-
ate; (E)-3-methyl-4-(2,6,6-trimethylcyclohex-2-en-1-yl)
but-3-en-2-one; (3aR,6S,7aS)-3a,4,5,6,7,7a-hexahydro-1H-
4,7-methanoinden-6-yl acetate; (Z)-3-methyl-2-(pent-2-en-
1-yl)cyclopent-2-enone; (Z)-3,4,5,6,6-pentamethylhept-3-
en-2-one; (Z)-1-(1-ethoxyethoxy) hex-3-ene (2E,6Z)-3,7-
dimethylnona-2,6-dienenitrile; (Z)-hex-3-en-1-yl methyl
carbonate; 3-(4-(tert-butyl)phenyl)-2-methylpropanal; 3,7-
dimethylocta-1,6-dien-3-ol; 3,7-dimethylocta-1,6-dien-3-yl
acetate; (4E)-9-hydroxy-5,9-dimethyl-4-decenal; 2-methyl-
4-oxo-4H-pyran-3-yl isobutyrate; ethyl 2-methylpentanoate;
2,6-dimethylhept-5-enal; 2-isopropyl-5-methylcyclohexa-
nol; 2-isopropyl-5-methylcyclohexanone; 1-((1S,8aS)-1,4,
4,6-tetramethyl-2,3,3a,4,5,8-hexahydro-1H-5,8a-methanoa-
zulen-7-yl) ethanone; undecan-2-one; methyl non-2-ynoate;
6,6-dimethoxy-2,5,5-trimethylhex-2-ene; 4-(4-methylpent-
3-en-1-yl)cyclohex-3-enecarbaldehyde; 2-(2-(4-methylcy-
clohex-3-en-1-yl) propyl)cyclopentanone; 2-methyl-6-
methyleneoct-7-en-2-yl acetate; (E)-methyl non-2-enoate;
(Z)-3,7,11-trimethyldodeca-1,6,10-trien-3-yl acetate; (Z)-3, 7-dimethylocta-2,6-dien-1-yl acetate; 6,8-dimethylnonan-2-
ol; (Z)-non-6-enal; 3-(4-isobutyl-2-methylphenyl) propanal;
4-(tert-pentyl)cyclohexanone; 2-ethyl-N-methyl-N-(m-
tolyl) butanamide; 2-methyl-4-methylene-6-phenyltetra-
hydro-2H-pyran; 2-cyclohexylidene-2-phenylacetonitrile;
2-cyclohexylidene-2-(o-tolyl) acetonitrile; 2,2-dimethyl-2-
pheylethyl propanoate; 1-methyl-4-(4-methylpent-3-en-1-
yl)cyclohex-3-enecarbaldehyde; 6-(sec-butyl) quinoline;
(E)-2-ethyl-4-(2,2,3-trimethylcyclopent-3-en-1-yl) but-2-
en-1-ol; 4-(4-hydroxyphenyl) butan-2-one; 2,2,5-trimethyl-
5-pentylcyclopentanone; 2,2,2-trichloro-1-phenylethyl
acetate); ROSALVA (dec-9-en-1-ol; (1-methyl-2-(5-methyl-
hex-4-en-2-yl)cyclopropyl)-methanol; 4-methylene-2-phe-
nyltetrahydro-2H-pyran; 2-(1-(3,3-dimethylcyclohexyl)-
ethoxy)-2-methylpropyl cyclopropanecarboxylate; 3-(4-
isobutylphenyl)-2-methylpropanal; 1-(spiro[4.5]dec-6-en-7-
yl) pent-4-en-1-one; (E)-5-methylheptan-3-one oxime; (E)-
6-ethyl-3-methyloct-6-en-1-ol; (E)-2-((3,5-dimethylhex-3-
en-2-yl)oxy)-2-methylpropyl cyclopropanecarboxylate;
1-methyl-4-propan-2-ylcyclohexa-1,4-diene; 1-methyl-4-
(propan-2-ylidene)cyclohex-1-ene; 2-(4-methylcyclohex-3-
en-1-yl) propan-2-yl acetate; 3,7-dimethyloctan-3-ol; 2,6-
dimethyloctan-2-ol; oxacyclohexadecan-2-one; (E)-tridec-
2-enenitrile; (E)-4-methyldec-3-en-5-ol; 2,2,5-trimethyl-5-
pentylcyclopentanone and (2,2-dimethoxyethyl)benzene
and 2-(2,4-dimethylcyclohexyl)pyridine).

26. An encapsulated composition obtained by the process
according to claim 1.

27. A consumer product comprising an encapsulated
composition according to claim 26.

28. A method of producing a consumer product which
comprises the step of;

including the encapsulated composition according to
claim 26 within the consumer product.

29. The consumer product according to claim 27, wherein
the consumer product is a fabric care product, a home care
product or a personal care product.

\* \* \* \* \*